United States Patent [19]

Merkl

[11] 3,959,093

[45] May 25, 1976

[54] ALUMINUM HYDRATES AND SALTS OF CARBOXYLIC ACIDS

[76] Inventor: George G. Merkl, 46 Sunset Court, Haworth, N.J. 07641

[22] Filed: May 13, 1974

[21] Appl. No.: 469,126

Related U.S. Application Data

[63] Continuation of Ser. No. 255,757, May 22, 1972, abandoned.

[52] U.S. Cl. ............................ 204/72; 204/59 QM; 260/448 R
[51] Int. Cl.$^2$ .................... C25B 3/00; C07F 5/06
[58] Field of Search ............ 204/59 R, 59 QM, 72; 136/86 A, 154; 260/448 R, 429.9, 436 R, 438.1, 430

[56] References Cited
UNITED STATES PATENTS

| | | | |
|---|---|---|---|
| 535,464 | 3/1895 | Schaeffer | 136/154 |
| 1,427,011 | 8/1922 | Orsolini | 136/154 |
| 1,863,254 | 6/1932 | Polin | 75/169 |
| 2,042,019 | 5/1936 | Pasternack et al. | 260/448 R |
| 2,275,211 | 3/1942 | Urbain et al. | 260/448 R |
| 3,574,607 | 4/1971 | Merkl | 75/134 |
| 3,578,439 | 5/1971 | Merriman | 75/169 |
| 3,856,841 | 12/1974 | Merkl | 260/448 A |

*Primary Examiner*—F. C. Edmundson
*Attorney, Agent, or Firm*—Arnold, White & Durkee

[57] ABSTRACT

Aluminum salts of a carboxylic acid selected from the group consisting of ascorbic acid, acetic acid, and citric acid are formed by contacting the carboxylic acid with activated aluminum. The activated aluminum is formed by combining highly pure aluminum with another metal which has an affinity for hydrogen in the presence of a proton source. Typically, the other metal can be gallium and the proton source can be hydrochloric acid. Included in the aluminum salts which can be formed are polymeric aluminum salts.

6 Claims, 3 Drawing Figures

ALUMINUM HYDRATES AND SALTS OF CARBOXYLIC ACIDS

This is a continuation of application Ser. No. 255,757, filed May 22, 1972, now abandoned.

CROSS REFERENCE

The co-pending application "Catalytic Electrode", Ser. No. 211,979, filed Dec. 27, 1971 provides numerous examples with the preparation of aluminum catalytic electrode.

PRIOR ART

Reference is had to co-pending application, "Metal Hydrates And Salts of Carboxylic Acids", Ser. No. 469,125 filed May 13, 1974.

The present invention relates to the method of forming a group of aluminum salts of selected carboxylic acids and to a new class of polymeric aluminum salts of selected carboxylic acids.

Generally, a metal salt of a carboxylic acid is a compound formed by a metal substituted for a hydrogen ion and is termed a metallic soap or simply a soap. Metallic soaps find wide application in industry. The common uses for soaps includes driers in paints, varnishes, and inks. In addition, the soaps are used as a mordant for dyes, curing hides, as a food nutrient, and of course, as a detergent.

The detergent properties of an aqueous soap solution are attributed to the structure of the soap. Typically, the soap includes a small hydrophilic cation and a larger anion which is heterpolar having a hydrophilic $COO^-$ group and a longer hydrophilic chain. At all concentrations, hydrophilic chains tend to concentrate at the surface of the solution and thereby tend to reduce surface tension. A better detergent appears to result for salts of carboxylic acids which are both soluble in water and in oil. The tendency for a soap solution to orientate the hydrocarbons at the surface also brings about a highly stable film forming property.

The prior art shows the existence of basic metal salts which relate to the polymeric aluminum salts as used in the present specification. A basic salt is characterized by the presence of a stoichiometric excess of metal relative to the number of equivalents of organic acid present therein based on the normal stoichiometry for the particular metal and organic acid. For example, if a normal aluminum salt has a ratio of aluminum to the acid of 1:1, the basic salt would have a higher ratio, e.g. 1.1:1, 2:1, 5:1, etc.

Basicsalts have also been referred to as being complex salts, superbase salts, and overbase salts. The term "polymeric salts", has been used in the German Auslegeschrift 1,243,415 since it was realized that the metal salt must be "sticking together" as a polymer in order to accommodate the extra metal atoms.

Prior art methods for preparing basic metal salts have included the use of metal alkoxides and in some cases promoters such as alcohol or oil. The products of the prior art methods have been highly impure and usually mixtures which have included foreign metal oxides and/or hydroxides in the product, along with an oil in many cases. The expression overbasing is probably due to the strongly basic solution characterizing the product. In further consideration, it is of interest to describe the known forms of aluminum acetate in order to contrast the polymeric aluminum acetate which will be described herein.

Aluminum acetate has been prepared in three forms: $Al(OH)_2(C_2H_3O_2)$, $Al(OH)(C_2H_3O_2)$, and $Al(C_2H_3O_2)_3$. The monoacetate and triacetate are soluble in cold water whereas the diacetate is only soluble in cold water upon being freshly prepared; otherwise, it is a white water insoluble powder. When the diacetate is heated, it looses acetic acid and an aluminum to oxygen bonding occurs to form an insoluble ccompound of disputed nature.

The aluminum salts prepared by the methods disclosed have many unique properties even when the aluminum salt corresponds to a known aluminum salt. For example, the aluminum salts prepared by the present method have extremely high purity and a particle size in the order of 15 to 50 Angstroms. The polymeric salts of the invention are water soluble, water clear, and have a pH in a range of about 4 to 5, which is close to the pH of the human skin which it about 4.1 to 4.2 pH. This later property is important for human contact since the polymeric aluminum salt will be non-irritating in contrast to basic salts of the prior art which have a pH in the order of 11.

THE ACTIVATED ALUMINUM

The present invention relates to methods of forming an aluminum salt of a carboxylic acid by contacting an activated aluminum with the carboxylic acid. In particular, the carboxylic acid is selected from the group consisting of acetic acid, ascorbic acid, and citric acid.

Methods of preparing activated aluminum are amply described in the aforementioned co-pending application but will be succinctly reported herein.

Activated aluminum is formed by diffusing a hydride forming metal into highly pure aluminum in the presence of a proton source. The hydride forming metal can be widely selected from such metals as cesium, indium, cadmium, sodium, gallium, and mercury. This hydride forming metal includes amalgams of indium, gallium, thallium, bismuth, silver, gold, and zinc, along with an alloy of indium and gallium.

An equal part of liquid alloy of indium and gallium in contact with a highly pure aluminum rod in the presence of hydrochloric acid will bring about a dramatic change in the physical and chemically properties of the aluminum rod. The alloy can have a mass from 1 to 3% of the rod. The rod can have a mass of about 100 grams and a diameter of a half inch.

It should be understood that the term "higly pure" means greater than 99% and that purities in the order of 99.9% and 99.99% are desirable.

The proton source, which is not at all limited to hydrochloric acid has a pH of about 0.2–4 and completely covers the aluminum rod.

One striking indication that activated aluminum has been formed is that the aluminum rod of the example will cause a rapid disassociation of water as compared to an untreated rod. An untreated rod may show the formation of only small bubbles, particularly at a freshly cut end, whereas the activated aluminum will show bubbles over its entire surface.

Under high magnification, activated aluminum has been observed to have innumerable tiny channels which are believed to account in part for the unusually chemical activity.

Activated aluminum has a tendency to form a coating over its surface after exposure to air. The coating can build up considerably in time and should be removed before using the activated aluminum. The coating can be removed with hot water or boiling it in hot water or with an acid such as hydrochloric acid.

A freshly prepared activated aluminum prepared with a gallium and indium alloy can be briefly dipped into anhydrous methyl alcohol, for example, for two or three minutes to avoid the formation of the coating.

Another example of preparing an activated aluminum is to place 100 grams of a 99.9% pure aluminum rod having a half inch diameter in about two grams of mercury and cover the rod with hydrochloric acid having about 4pH. The vessel in this and other cases should be non-reactive material, such as glass. After most of the mercury has been absorbed an activated aluminum has been formed. More than two grams of mercury can be used but the reaction should be stopped when about two grams of mercury have been absorbed. Pouring cold water into the solution to dilute the acid greatly will virtually stop the reaction so that the rod can be removed. If the rod is removed to stop the reaction, overheating of the rod occurs and the channels tend to contract and squeeze the mercury out.

When an acid such as hydrochloric acid has been used in the preparation of an activated aluminum, it is desirable to purge the activated aluminum of residual hydrochloric acid so as not to disturb the subsequent formation of a metal salt. One way of cleansing the activated aluminum is to run very hot water over the activated aluminum to thoroughly wash out the hydrochloric acid or other acid, depending upon what is used. In some cases, it may be convenient to use a carboxylic acid to form the activated aluminum particularly when the same carboxylic acid will be used subsequently. Because many of the carboxylic acids are weak acids it may be necessary to heat the carboxylic acid when forming the activated aluminum. The added heat should not be sufficient to decompose the carboxylic acid. Naturally, if the same carboxylic acid is used to prepare the activated aluminum and to form the metal salt the need not be washed at all.

SUMMARY OF THE INVENTION

The present invention makes use of the unique properties of an activated aluminum by forming an aluminum salt of a carboxylic acid through the contacting of the activated aluminum with a carboxylic acid. The carboxylic acids being water soluble lend themselves to the formation of a polymeric aluminum salt; the activated aluminum and carboxylic acid are contacted in the presence of an excess amount of water.

Combining the water soluble carboxylic acid, an activated aluminum, and water where appropriate in a stoichiometric ratio as dictated by the formula of a desired aluminum salt will produce the desired aluminum salt.

THE INVENTION

In all methods of preparing an aluminum salt, it will always be advantageous to use either a freshly prepared activated aluminum or one freshly treated to remove any coating. In the samples wich follow freshly activated aluminum is always intended.

The specific preparation of a polymeric aluminum salt is usually carried out by the combination of the activated aluminum, water soluble carboxylic acid, and an excess of water at room temperature or at a somewhat lower temperature. The pH of the solution is preferably less than 4.2.

In the examples which follow, it is to be understood that the invention is not to be limited to just these examples and variations within the scope and spirit of the disclosure herein will be apparent to persons skilled in the art.

EXAMPLE 1

To form a polymeric aluminum acetate the formula $Al_2(OH)_5C_2H_3O_2 \cdot 2H_2O$ is a good guide for the mass ratio of the activated aluminum and acetic acid; and excess of water is added to assure the formation of the polymeric aluminum salt. About three times the amount of water predicated on the stoichiometry is satisfactory. The actual water of crystallization or even the formula can vary. The water of crystallization can easily range from one to three while the aluminum need only be greater than about one atom per mol. Nevertheless, the formulas given herein provide a rational basis for apportioning the constituents. No limitation should be inferred from the presentation of model formulas for polymeric aluminum salts. Then, 60 grams of acetic acid, 54 grams of activated aluminum, and 366 grams of water are combined in a beaker and left until the activated aluminum has been substantially consumed, which can taken about two weeks at room temperature. Room temperature or somewhat cooler is preferred. During the reaction hydrogen bubbles will be seen rising from the activated aluminum to the surface of the liquid. As polymerization progresses, the viscosity of the solution increases as evidenced by a slower rise of the bubbles and the larger size of the bubbles needed to break free from the surface of the activated aluminum.

EXAMPLE 2

A polymeric aluminum citrate can be made based on the model formula $Al_2(OH)_5C_6H_7 \cdot 2H_2O$, again with an excess of water. The constituents are 192 grams of citric acid (anhydrous), 54 grams of activated aluminum and 499 grams of water. The reaction is run at room temperature until the activated aluminum has been substantially consumed.

EXAMPLE 3

A polymeric aluminum ascorbate is based on the stoichiometry in accordance with the model formula. $Al_2(OH)_5CH_2OHCHOHCHCOH=COCOO.2-H_2O$. Excess water is used. The constituents are 176 grams of ascorbic acid, 54 grams of activated aluminum, and 483 grams of water. The reaction is run at room temperature until the activated aluminum has been substantially consumed.

Figure 1:
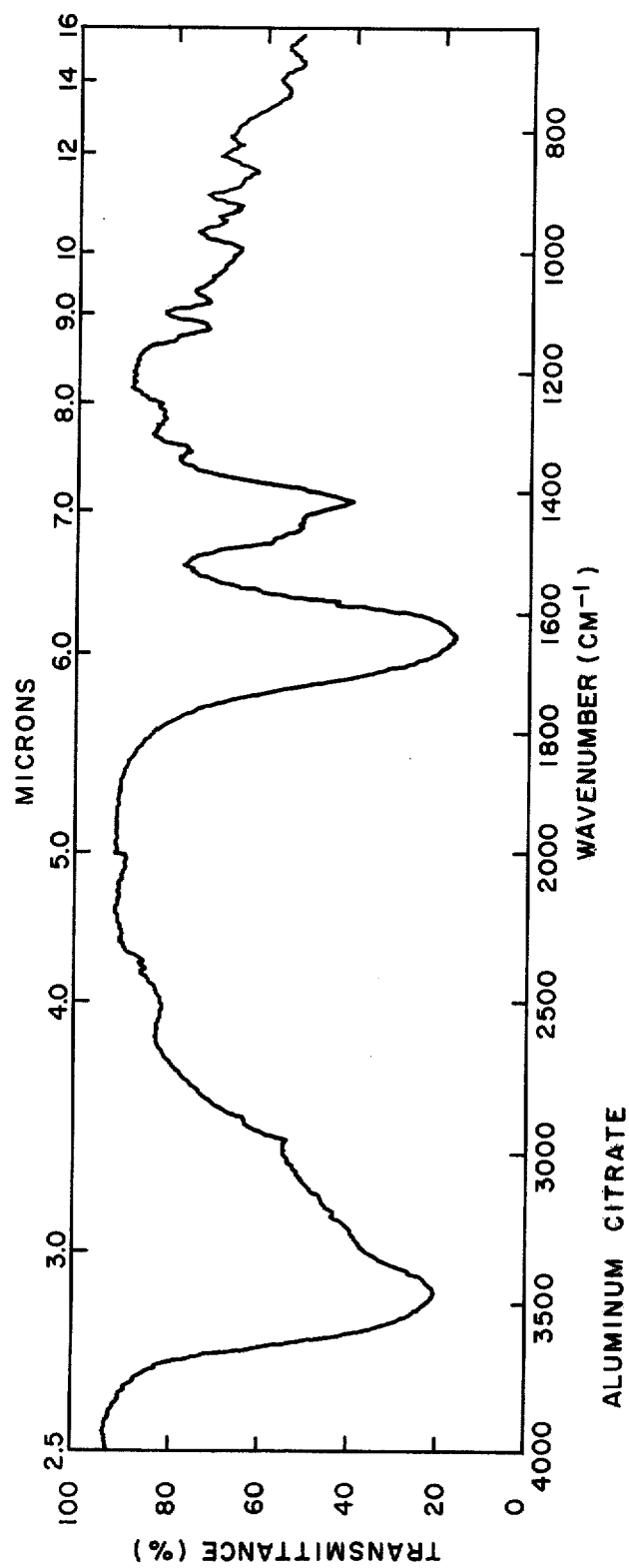
FIGS. 1-3 are infrared spectra responses corresponding to three polymeric aluminum salts of the present invention.
Figure 2:
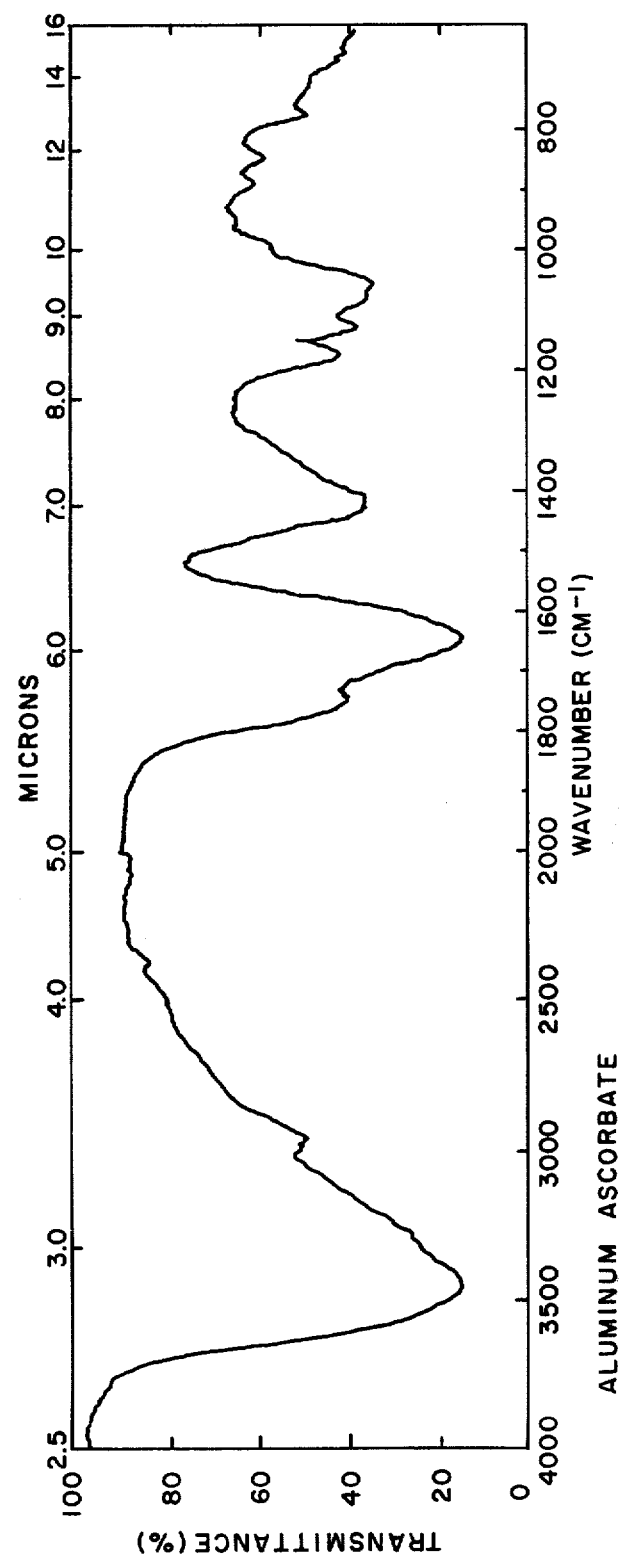
Figure 3:
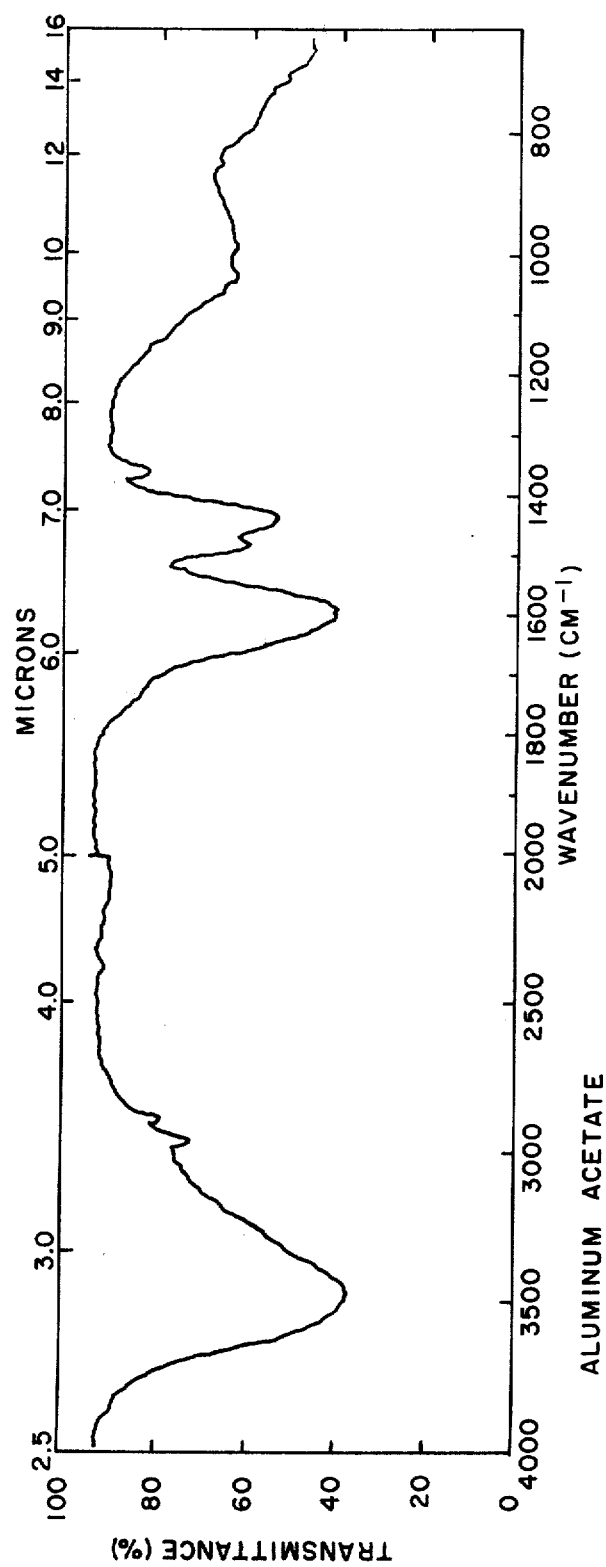

The polymers of EXAMPLES 1-3 are unique in many ways, including very high purity and novel structure. FIGS. 1-3 show infrared spectra of the polymers of aluminum citrate, aluminum ascorbate, and aluminum acetate, respectively. The infrared spectra graphs of FIGS. 1-3 are remarkably "clean"; that is, are characterized by an absence of numerous valleys and peaks resulting from the presence of impurities found in prior art formulations of polymeric aluminum salts.

Each sample for the infrared spectra measurement was prepared in a well-known procedure of mixing about 1% by weight of the compound to be tested with potassium bromide and then forming a disc under a vacuum.

It universally is recognized that infrared absorption spectrum of a compound uniquely identifies the compound, much like a fingerprint identifies an individual, and the infrared spectra also provides insight to the structure of the compound.

A glance at the figures indicates similarities between the variations such as valleys and flat regions. The flat regions or small shoulders in the figures generally correspond to minor absorption levels but have some significance when viewed with respect to corresponding shoulders of variations in other figures. Table 1 presents a correlation of variations which appear in the figures. In some cases a variation is a valley but the correlated variation in another figure is only a slight dip. Some further comment on Table 1 follows. The comments which follow are not intended to be a limitation but merely to be informative.

Variation number 1 corresponds to O—H stretching and the magnitude which appears in the drawings tends to verify the polymeric form of the compounds. Variation 2 is found in chelates and may be due to track ions or the like. It will be noted that aluminum acetate in FIG. 3 shows two variations. Variation 3 corresponds to region which is usually associated with a response to broad multiplex, no response appears evident for the ascorbate or the acetate. Variation 4 which appears in all the figures does not seem to relate to any well known absorption response, on the other hand variations 5-3 are well known to occur for metal salts. Some splitting or variation within a response region occurs for the metal salts of heavier hydrocarbons. Variation 9 may be due to free oxygen trapped within the chelate structure of the polymers. Variations 10 and 11 occur within regions known to show absorption for organometallic compounds. Due to the novelty of organoaluminum compounds not very much data is available.

The depth of the valley in the region of 1650 to 1750 cm$^{-1}$ has particularly important significance in that the valley in this region substantiates the proposed polymeric structure as set forth above. It is known that the organic acid will show H bonds in this region as will aluminum to hydrogen bonding. As a matter of fact, it has been noted in the prior art that an organic acid will show about a medium absorption depth in this region as well as a compound having only aluminum to hydrogen bond. Polymeric compounds of the type shown in the figures bear out the expectation that the combination of hydrogen bonding in the organic part of the compound and the hydrogen bonding in the inorganic compound will produce an absorption depth about twice of either the absorption depths along.

It should be understood that it is the gross variation of each of the figures which has significance and bearing to the respective polymeric compounds.

TABLE 1

Some correlated variations present in the infrared spectra of FIGS. 1-3

| Variation Number | Aluminum citrate CM$^{-1}$ | Aluminum ascorbate CM$^{-1}$ | Aluminum acetate CM$^{-1}$ |
|---|---|---|---|
| 1. | 3460 | 3445 | 3465 |
|  |  |  | 2960 |
| 2. | 2960 | 2960 | 2880 |
| 3. | 2500 | — | — |
| 4. | 2380 | 2380 | 2380 |
|  |  | 1750 | 1765 |
| 5. | 1640 | 1645 | 1590 |
|  | 1455 |  | 1485 |
| 6. | 1415 | 1420 | 1440 |
|  | 1330 |  |  |
| 7. | 1270 | — | 1360 |
|  |  | 1170 |  |
|  |  | 1130 |  |
|  |  | 1080 | 1140 |
| 8. | 1125 | 1055 | 1035 |
|  | 990 | 990 |  |
|  | 940 | 950 |  |
|  | 920 | 890 | 930 |
| 9. | 860 | 850 | 850 |
|  | 820 |  |  |
| 10. | 730 | 770 | 760 |
| 11. | 680 | 670 | 660 |

EXAMPLE 4

The polymeric aluminum acetate can be made in a much shorter period of time by utilizing approximately six times the amount of activated aluminum that is, about 324 grams of activated aluminum positioned at the bottom of the vessel as to permit the liquid to move past the rods freely and letting the mixture stand for about 24 hours. After about 24 hours, a sample of the mixture should be checked to determine the ratio of the aluminum present. If the ratio is approximately 1.7 to 1 or as high as 1.9 to 1, then the mixture can be placed on a hot plate and heated for about 10 minutes to finish the reaction. The reaction should be stopped for a titrated metal ratio of about 2 to 1. For that ratio, the liquid should be poured off immediately to prevent the activated aluminum from carrying the reaction further.

EXAMPLE 5

The procedure in EXAMPLE 4 can be applied for the case of EXAMPLE 2 in order to produce a polymeric aluminum citrate in a shorter time.

EXAMPLE 6

In the procedure of EXAMPLE 4, can be applied to the preparation of the polymeric aluminum ascorbate in Example 3 in order to shorten the preparation time.

It is convenient to pour off the polymeric metal salts of EXAMPLES 1 to 6 and permit them to gel or solidify. The time for solidification depends upon the amount of excess water. If it is found that the amount of water in the reaction results in a very long time for gelling, it may be desirable to use somewhat less water in the reaction. Too little water tends to permit the formation of ordinary aluminum salts. Both the polymeric metal salt solution and solid are water clear.

Turning now to the preparation of ordinary stoichiometric aluminum salts of carboxylic acids, the following examples are provided.

EXAMPLE 7

To prepare aluminum monoacetate, $Al(OH)_2(C_2H_3O_2)$, combine 60 grams of acetic acid, 27 grams of aluminum and 34 grams of water. The mixture should be left at room temperature until the activated aluminum has been substantially consumed.

EXAMPLE 8

To prepare aluminum diacetate, $Al(OH)(C_2H_3O_2)_2$, combine 120 grams of acetic acid, 27 grams of activated aluminum, and 18 grams of water at room temperature. The mixture should be left until the activated aluminum has been substantially consumed.

EXAMPLE 9

To prepare aluminum triacetate, $Al(C_2H_3O_2)$, combine 180 grams of acetic acid, and 27 grams of activated aluminum at room temperature. The mixture should be left until the activated aluminum has been substantially consumed.

I claim:

1. A method of preparing an aluminum-carboxylic acid compound which comprises:

reacting by contacting, in the presence of water:
  a. activated aluminum comprising high purity metallic aluminum permeated with a metal selected from mercury, indium, gallium and alloys of indium and gallium; with
  b. a carboxylic acid selected from acetic acid, ascorbic acid and citric acid; whereby the aluminum of said activated aluminum is consumed in reaction with said carboxylic acid, thereby forming said aluminum-carboxylic acid compound.

2. The method of claim 1, wherein said aluminum has a purity of at least about 99.99% by weight.

3. The method of claim 1, wherein said activated aluminum and carboxylic acid are reacted in the presence of an excess of water, based upon the water of crystallization of the formed aluminum-carboxylic acid compound.

4. The method of claim 3, wherein the reaction is carried out at room temperature or below.

5. The method of claim 3, wherein the pH of the reaction medium is less than 4.2.

6. The method of claim 1, wherein the activated aluminum comprises highly pure aluminum permeated with from 1 to 3% by weight of an alloy of indium and gallium.

* * * * *